United States Patent
Garth et al.

(10) Patent No.: US 9,949,860 B2
(45) Date of Patent: Apr. 24, 2018

(54) BRACE HAVING ELASTIC AND INELASTIC PORTIONS

(71) Applicant: Aspen Medical Partners, LLC, Irvine, CA (US)

(72) Inventors: Geoffrey Garth, Long Beach, CA (US); Steven Burke, Huntington Beach, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 304 days.

(21) Appl. No.: 14/641,819

(22) Filed: Mar. 9, 2015

(65) Prior Publication Data

US 2015/0250634 A1 Sep. 10, 2015

Related U.S. Application Data

(60) Provisional application No. 61/949,934, filed on Mar. 7, 2014.

(51) Int. Cl.
*A61F 5/02* (2006.01)

(52) U.S. Cl.
CPC ........ *A61F 5/028* (2013.01); *A61F 2250/001* (2013.01)

(58) Field of Classification Search
CPC .......... A61F 5/028; A61F 5/024; A61F 5/026; A61F 13/14; A61F 5/03; A61F 5/3784; A61F 5/3769; A61F 5/3792; A47D 15/008
See application file for complete search history.

(56) References Cited

U.S. PATENT DOCUMENTS

| | | | |
|---|---|---|---|
| 2,132,971 A | 10/1938 | Roques | |
| 2,147,166 A | 2/1939 | Kops | |
| 2,289,302 A | 7/1942 | Bradshaw | |
| 2,306,246 A | 12/1942 | Davis | |
| 2,306,914 A | 12/1942 | Smith, Jr. | |
| 2,311,166 A | 2/1943 | Fregeolle | |
| 2,411,175 A | 11/1946 | Wagler | |
| 3,154,072 A * | 10/1964 | Mack | A61F 5/028 128/117.1 |
| 3,747,374 A | 7/1973 | Meyer | |

(Continued)

FOREIGN PATENT DOCUMENTS

| | | |
|---|---|---|
| CA | 417263 | 12/1943 |
| CA | 420867 | 6/1944 |

(Continued)

OTHER PUBLICATIONS

Vertebradyn-Strong, Sporlastic GMBH, http://www.sporlastic.de/de/main/platinum/07425.html, downloaded on Apr. 9, 2015.

(Continued)

*Primary Examiner* — Ophelia A Hawthorne
(74) *Attorney, Agent, or Firm* — Fish IP Law, LLP

(57) ABSTRACT

Braces having elastic portions that can be made effectively inelastic, based on a level of comfort or support desired by a user, via an inelastic tightening mechanism are disclosed. Some contemplated braces have lumbar supports that are at made at least in part of an elastic material, and inelastic tightening systems that extend across the elastic material and can decrease the effective elasticity of the elastic material to provide greater support.

20 Claims, 2 Drawing Sheets

(56) References Cited

U.S. PATENT DOCUMENTS

| | | | |
|---|---|---|---|
| 3,927,665 | A | 12/1975 | Wax |
| 4,794,916 | A | 1/1989 | Porterfield et al. |
| 5,388,274 | A | 2/1995 | Glover et al. |
| 5,421,809 | A | 6/1995 | Rise |
| 5,484,395 | A | 1/1996 | DeRoche |
| 5,643,184 | A | 7/1997 | Toso |
| 5,722,940 | A | 3/1998 | Gaylord, Jr. et al. |
| 5,833,638 | A | 11/1998 | Wilson |
| 6,082,148 | A | 7/2000 | Wakai et al. |
| 6,923,779 | B1 | 8/2005 | Choiniere |
| 7,025,737 | B2 | 4/2006 | Modglin |
| 7,449,006 | B2 | 11/2008 | Wolanske |
| 8,328,742 | B2 | 12/2012 | Bledsoe |
| 2003/0195449 | A1 | 10/2003 | Coleman |
| 2004/0139974 | A1 | 7/2004 | Schwenn et al. |
| 2005/0059917 | A1 | 3/2005 | Garth et al. |
| 2005/0150258 | A1 | 7/2005 | Mitchell et al. |
| 2009/0118655 | A1 | 5/2009 | Wang |
| 2009/0306570 | A1 | 12/2009 | Bauerfeind |
| 2010/0228170 | A1 | 9/2010 | Imai |
| 2012/0253251 | A1 | 10/2012 | Thornton |
| 2013/0158457 | A1 | 6/2013 | Garth et al. |
| 2013/0160328 | A1 | 6/2013 | Hatfield et al. |
| 2013/0237891 | A1* | 9/2013 | Fryman ............... A61F 5/02 602/19 |
| 2013/0333706 | A1 | 12/2013 | Bauerfeind |
| 2015/0328033 | A1 | 11/2015 | Ingimundarson et al. |
| 2015/0328035 | A1* | 11/2015 | Idowu ............... A61F 5/03 602/19 |

FOREIGN PATENT DOCUMENTS

| | | |
|---|---|---|
| CN | 2333372 | 8/1999 |
| CN | 101437682 | 8/2012 |
| FR | 2356755 | 1/1978 |
| GB | 539759 | 9/1941 |
| GB | 2070656 | 9/1981 |
| JP | 11-104159 | 4/1999 |
| JP | 2003013347 | 1/2003 |
| JP | 3094642 | 7/2003 |
| JP | 2007-105308 | 4/2007 |
| JP | 4762053 | 8/2011 |
| JP | 2013138823 | 7/2013 |
| JP | 2014212864 | 11/2014 |
| KR | 2002085750000 | 1/2001 |
| KR | 200243883 | 8/2001 |
| WO | 2014037213 | 3/2014 |
| WO | 2015134997 | 9/2015 |

OTHER PUBLICATIONS

Vertebradyn-Vario, Sporlastic GMBH, http://www.sporlastic.de/en/mainiplatinum/07420.html, downloaded on Apr. 9, 2015.
Comprehensive LSO, Cybertech Medical, http://www.cybertechmedical.com/products/LSO_8_comprehensive_lso.php, downloaded on Apr. 9, 2015.
Comffit Lite Back Support, Sportstek, https://www.sportstek.net/comffit-lite.htm, downloaded on Apr. 9, 2015.
SacroLoc, Bauerfeind, http://www.bauerfeind.com/b2c/bauerfeind-b2c-us/en/USD/PRODUCT/BACK-BRACES-BY-LUMBOTRAIN-AND-SACROLOC/SacroLoc%C2%AE/p/YPBF_ORW_SACROLOC, downloaded on Apr. 9, 2015.
Cybertech Pathway LS, Cybertech Medical, http://www.cybertechmedical.com/products/LSO_5_pathway_ls.php, downloaded on Apr. 9, 2015.
Donjoy Lumboforce, product brochure, DJO Global, Aug. 2012.
Orthesen & Bandagen, Donjoy, Lumboforce, DJO Global, Apr. 9, 2015.

* cited by examiner

BRACE HAVING ELASTIC AND INELASTIC PORTIONS

This application claims priority to U.S. Provisional Application Ser. No. 61/949,934, filed Mar. 7, 2014. This and all other extrinsic materials identified herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is orthotic devices.

BACKGROUND

The background description includes information that may be useful in understanding the present invention. It is not an admission that any of the information provided herein is prior art or relevant to the presently claimed invention, or that any publication specifically or implicitly referenced is prior art.

Efforts have been made to provide flexible back support braces that a user could comfortably wear for everyday general use. For example, the Australian Comffit™ Lite Back Support brace is a lower back brace that attempts to provide comfort and support to wearers by including vertically and horizontally stretchable portions sewn to a back portion can only be stretched horizontally. Four flexible plastic stays are sewn vertically throughout the brace to assist with lumbar compression.

However, recent research shows that the effectiveness of a lower spine brace in relieving lower back pain depends at least in part on how well the brace improves trunk stability. As inelastic braces are more effective in augmenting trunk stiffness, thereby allowing overtaxed lower back muscles to relax, inelastic braces are often preferred over elastic braces.

Unfortunately, inelastic braces can be very restrictive for wearers, especially for those that require relief when performing tasks, work, or other physical activities where mobility is beneficial. Therefore, some efforts have unsuccessfully been made to produce a brace that provides the comfort of an elastic brace with the support of an inelastic brace.

For example, U.S. Pat. No. 5,833,638 to Nelson provides a brace including elastic and inelastic materials. As another example, U.S. Pat. No. 7,025,737 to Modglin provides a spinal brace having flexible materials incorporating rigid supports. Unfortunately, the elastic portions of these braces remain consistently elastic in all configurations and the trunk stability associated with an inelastic brace is largely lost.

It has yet to be appreciated that a brace could adjust from a generally elastic brace to a generally inelastic brace depending on the desired comfort or support required. Thus, there is still a need in the art for improved braces that provide relief without being overly restrictive.

SUMMARY OF THE INVENTION

The inventive subject matter provides apparatus, systems and methods in which braces having inelastic and elastic portions can provide support to a lower spine of a wearer while also providing increased comfort and ease of use. More specifically, a brace of the inventive subject matter includes a lumbar support having a portion that is sufficiently elastic such that the support and the portion can be adjusted to conform to a wearer's body. Additionally, a corresponding inelastic tightening system extends across at least some of the elastic portion, and can be adjusted to provide a necessary or desired force to the wearer's body when the brace is worn. Viewed from another perspective, an elastic portion of the lumbar support can effectively be made less elastic or even inelastic, via an adjustment of the tightening system.

In some aspects of the inventive subject matter, the lumbar support is coupled to (and disposed between) left and right lateral supports. The left and right lateral supports are typically inelastic. However, it is contemplated that in some embodiments one or more of the lateral supports could be elastic in whole or in part. The three supports, in combination, could be configured to wrap around the lower torso of a wearer. For example, the lumbar support could be sized and dimensioned to cover a lower back portion of the wearer and the lateral supports could be sized and dimensioned to wrap around the waist of the wearer and fasten to one another.

The inelastic tightening system that extends across the elastic portion of the lumbar support can advantageously be tightened or loosened to adjust a force that is applied to the lower back of the wearer. Viewed from a different perspective, upon tightening, the inelastic tightening system can reduce the effective elasticity of the elastic portion since the elastic portion's elasticity is limited by the lack of elasticity of the tightened inelastic system extending across it.

From a methods perspective, a brace of the inventive subject matter could be wrapped around the waist of a user, stretching the elastic portion to conform to the shape of the user and provide a desired fit. The inelastic tightening mechanism can then be tightened until a desired amount of force is placed on the user's body, and fastened in place. Throughout use, when the user desires a more comfortable fit with greater effective elasticity, or a tighter fit with less effective elasticity, the tightening mechanism can be loosened or tightened until the desired fit is obtained.

Thus, as further described in the detailed description, braces of the inventive subject matter allow a user to determine or select the overall elasticity of a brace, and adjust the brace throughout the day based on a desired level of comfort and support through a simple adjustment of the inelastic tightening mechanism. For example, a user may wish to have a more elastic brace when initially wrapping the brace around his or her torso (e.g., for fitting of the brace) to allow the brace to conform to the wearer. Additionally or alternatively, the user may wish to have a more inelastic brace when running or engaging in other physical activities so that brace provides a higher level of support. The user could simply tighten the inelastic tightening mechanism to reduce the effective elasticity of the elastic portion and the brace as a whole. Additionally or alternatively, the user may wish to have a more elastic brace when sitting down, working at a desk or relaxing. The user could loosen the inelastic tightening mechanism so that more of the elastic portion's natural elasticity is realized.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1b illustrates the inner surface of the brace of FIG. 1a.

DETAILED DESCRIPTION

Figure 1A:
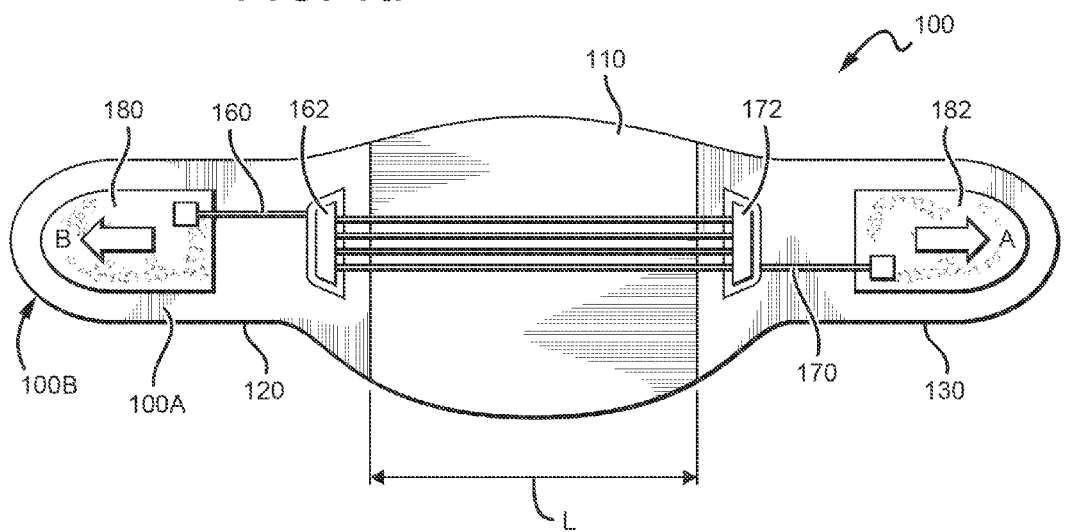
FIG. 1a illustrates the outer surface and tightening system of a brace of the inventive subject matter.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter provides braces that include an inelastic tightening system extending over an elastic material, wherein the inelastic tightening system is configured to reduce an effective elasticity of the elastic material when tightened. Such braces advantageously allow a user to effectively adjust a brace's general elasticity throughout the day depending on the desired level of comfort and support required.

As used herein, the term "elastic portion" refers to any portion made of a material that allows the portion to stretch to at least 110% (e.g., 110%, 115%, 120%, 130%, 140%, 150%, 175%, 200%, etc.) beyond its original length, and return to within 98% (e.g., 98%, 99%, 100%, etc.) of its original length. Exemplary elastic materials include, among other things, certain types of Lycra™, rubber, Nylon™, polyester-cotton blend, spandex-cotton blend, and spandex. One should appreciate that a "length" could refer to a side-to-side length, a top-to-bottom length, a diagonal length, or any other suitable length. All other portions or panels falling outside of the scope of this definition of "elastic portion" are considered "inelastic" portions or panels.

As used herein, the term "effective elasticity" of an elastic portion refers to the stretchability of the elastic portion when a brace including the elastic portion is worn in combination with an inelastic tightening system in a given configuration. The effective elasticity of the elastic portion cannot be increased by the inelastic tightening system, but could be reduced by tightening the inelastic tightening system from a first configuration to a second tightened configuration. Viewed from another perspective, a shorter length of the inelastic tightening system extends across the elastic portion in the tightened configuration, which reduces the effective elasticity of the elastic portion when the brace is worn since the elastic portion's effective elasticity is limited by the inelastic system extending across it.

An elastic lumbar support could be made in whole or in part of an elastic material, and could be directly or indirectly coupled to one or more inelastic supports. Preferably the elastic material of the lumbar support is at least 3 inches wide, more preferably at least 5 inches wide, and more preferably at least 7 inches wide. Additionally or alternatively, the elastic material of the lumbar support can be at least 3 inches in length, at least 5 inches in length, at least 7 inches in length or even greater. In some preferred embodiments, the elastic lumbar support is coupled to first and second lateral supports made of an inelastic material such that all or substantially all portions of the brace can be made effectively inelastic (as further described below) when worn by a wearer with a tightening system configuration that prevents a stretching of the elastic lumbar support panel. In other contemplated embodiments, a brace can comprise 2, 3, 4, or even 5 or more elastic portions and corresponding tightening mechanisms. Viewed from another perspective, a brace of the inventive subject matter could advantageously allow a user to arrange a tightening system in various configurations that increases or decreases an effective elasticity of a brace as desired.

Additionally or alternatively, a brace can comprise one or more elastic portions that do not have corresponding tightening mechanisms (e.g., elastic portions that remain consistently elastic).

It should be appreciated that in embodiments where the lumbar support is made of an elastic material, the elastic material would be elastic regardless of the specific configuration of the tightening system. However, when an inelastic tightening system is provided that extends across a length of the elastic material, it is contemplated that a stretching of the lumbar support across a lumbar region of the wearer (when worn) could be prevented to a desired degree by adjusting the tightening system from a first (e.g., loose) configuration to a second (e.g., tight) configuration, thereby making the lumbar support temporarily and effectively inelastic.

Figure 1B:
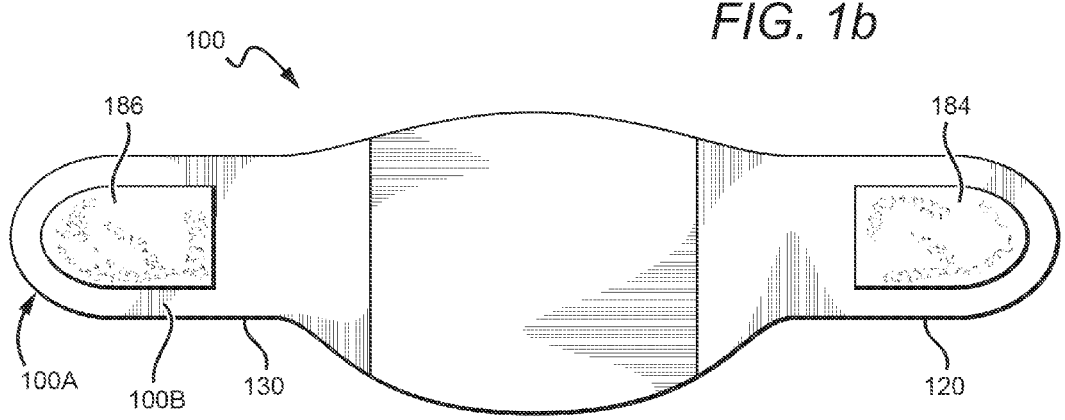

FIGS. 1A-1B illustrate outer and inner surfaces (100A, 100B, respectively) of an exemplary brace of the inventive subject matter. Brace 100 comprises an elastic lumbar support 110 disposed between first lateral support 120 and second lateral support 130. The lumbar support is configured to extend across a sagittal plane and be applied to a lower back of the wearer. The first and second lateral supports each include two fasteners (180,184 on opposite surfaces of the first panel; 182, 186 on opposite surfaces of the second panel) and are preferably configured to wrap around the waist of the wearer and fasten to one another at or near the abdomen.

In the embodiment shown, first fastener 180 and fourth fastener 186 are complementary hook and loop fasteners, and second fastener 182 and third fastener 184 are complementary hook and loop fasteners. However, all suitable fasteners are contemplated, including for example snaps, buttons and clasps, especially fasteners that allow for a brace to comfortably fit users of different shapes and sizes.

When wrapping brace 100 around a lower torso of the wearer, elastic lumbar support 110 can advantageously be stretched across the lumbar region of the wearer to provide a desired tight fit. For example, it is contemplated that the elastic portion is stretchable by at least 10% (i.e., to 110% of an original un-stretched length), at least 20%, at least 30% or even at least 50% or more in length. Viewed from another perspective, the elastic portion can be stretched to increase from its original length at rest to X times the original length when the tightening system is in a first configuration (e.g., not used), and can be stretchable to increase from the original length to no more than (0.1X, 0.2X, 0.3X, 0.4X, 0.5X, 0.6X, 0.7X, 0.8X or 0.9X times the original length) when the tightening system is in a more tightened configuration. It is contemplated that the tightening system could be configurable between an unused configuration and 1, 2, 3, 4, 5, or even more different tightened configurations.

Additionally, brace 100 includes inelastic first and second cords 160 and 170, each of which thread through first and second cord guides 162, 172 disposed on first and second lateral supports, respectively. First cord 160 has a first end that exits first cord guide 162 and can be pulled in direction B to tighten brace 100 when worn. Second cord 170 has a second end that exits second cord guide 172 and can be pulled in direction A, preferably simultaneously with first cord 160, to tighten brace 100. It is contemplated that pulling first and second cords beyond a threshold point in directions B and A, respectively, can shorten an exposed length L of lumbar support 110.

It is contemplated that first and second cords could each comprise pull tabs including or coupled with a fastener (e.g., snaps, hook and loop, buttons, hooks, etc.), wherein the fastener allows the cord to be fastened to different portions of at least one of the first lateral support, the second lateral support and the lumbar support.

All commercially suitable inelastic tightening systems are contemplated, including for example, a single cord based system or an inelastic fabric that is sized and dimensioned to extend across an elastic portion of a brace and fasten with corresponding fasteners of first or second lateral supports. Some exemplary tightening systems are described in U.S. Patent Publication no. 2013/0237891 and U.S. Patent Publication No. 2013/0158457, and other examples include other cord systems and even non-cord systems.

Preferred tightening systems are adjustable between at least a first and second configuration, wherein the lumbar support is capable of stretching at least 110%, at least 115%, at least 120%, at least 150%, or even at least 200% (two times) more when worn by a wearer with the tightening system in a first loosened configuration than when worn by the wearer with the tightening system in a second tightened configuration. In some embodiments, the tightening system is additionally adjustable between second and third configurations, wherein the lumbar support is capable of stretching at least 110%, at least 115%, at least 120%, at least 150%, or even at least 200% more when worn by the wearer with the tightening system in a second tightened configuration than when worn by the wearer with the tightening system in a third, more tightened configuration.

While the disclosure herein is generally directed towards braces having an inelastic back support panel, it should be appreciated that one or more elastic portions could be disposed along any suitable portion of any suitable orthosis device having an inelastic tightening mechanism. For example, it is contemplated that a lower back brace could comprise an elastic portion sized and dimensioned for placement along a side or front portion of a wearer. As another example, it is contemplated that a knee brace could have an elastic portion sized and dimensioned for placement along a knee cap of the wearer, and an inelastic tightening strap could be disposed across the elastic portion and tightened to reduce the effective elasticity of the knee cap portion.

Figure 2A:
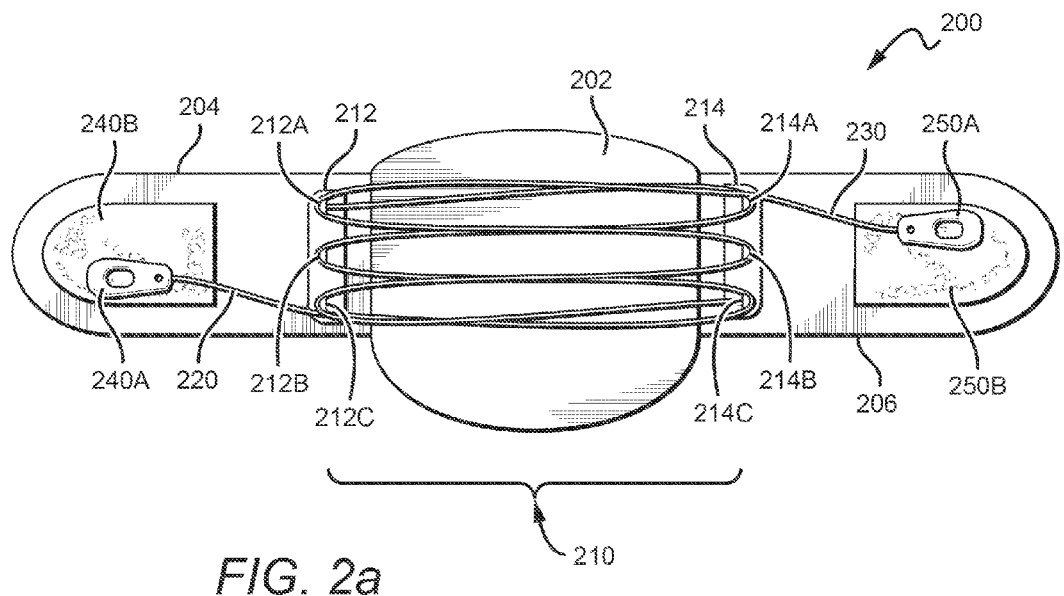
FIG. 2a illustrates the outer surface of another brace of the inventive subject matter having an exposed tightening mechanism.
Figure 2B:
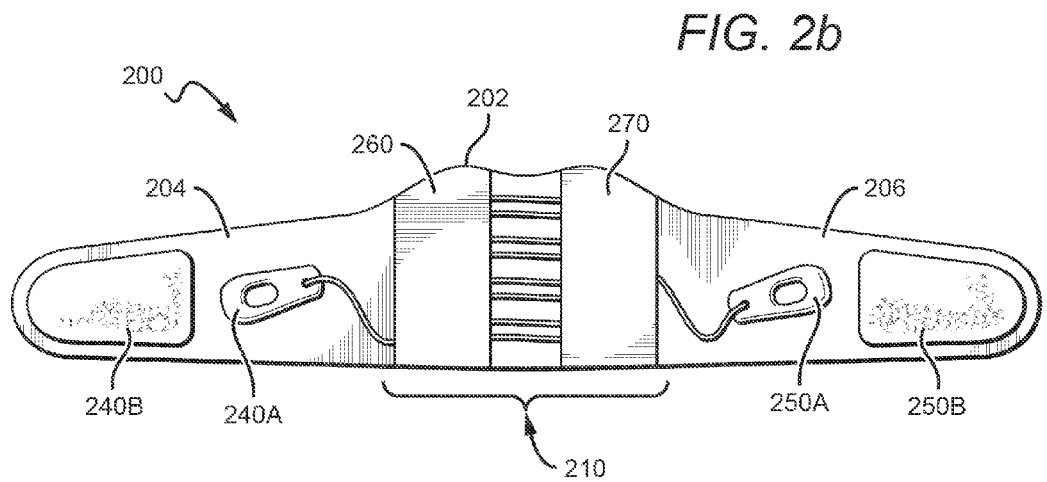
FIG. 2b illustrates the outer surface of the brace of FIG. 2a having a partially covered tightening mechanism.

FIGS. 2A-2B illustrate another embodiment of a brace 200 of the inventive subject matter. Brace 200 comprises an elastic lumbar support 202 disposed between a first lateral support 204 and second lateral support 206, and is configured to wrap around a portion of a wearer's body. The elastic lumbar support 202 allows a user to adjust an overall elasticity of the brace when worn, while the first and second lateral supports 204 and 206 include one or more fasteners that allow a user to temporarily lock the brace in the desired configuration.

Brace 200 also includes a tightening mechanism 210 that further allows the user to adjust the overall elasticity of the brace when worn. Tightening mechanism 210 includes a first cord guide base 212 disposed on first lateral support 204 and having cord guide lobes (212A, 212B, 212C) a second cord guide base 214 disposed on second lateral support 206 and having cord guide lobes (214A, 214B, 214C), a first cord 220 that threads through a subset of the cord guide lobes of first and second cord guide bases 212 and 214 and extends out of first cord guide base 212, and a second cord 230 that threads through a subset of the cord guide lobes of first and second cord guide bases 212 and 214 and extends out of second cord guide base 214.

First and second cords 220 and 230 of tightening mechanism 210 can be pulled in opposite directions when brace 200 is worn to reduce an effective elasticity of lumbar support 202. Once a desired effective elasticity is achieved, fasteners of pull tabs 240A and 250A of first and second cords 220 and 230 can be engage with at least one of fastener 240B of first lateral support 204 and fastener 250B of second lateral support 206. Once brace 200 is fastened around a torso of the wearer, a user could pull the cords (e.g., via first and second pull tabs 240A and 250A) until a desired elasticity of the lumbar support 202 or brace 200 generally is achieved. Furthermore, the user could fasten one or more of the pull tabs 240A and 250A in place, for example, where the first pull tab's fastener is configured to engage with fastener 240B of the first lateral support 204, and the second pull tab's fastener is configured to engage with fastener 250B of the second lateral support 206. Additionally or alternatively, when the user desires a more elastic fit or a more inelastic fit, it is contemplated that the user can disengage the fasteners of pull tabs 240A and 250B, tighten or loosen the inelastic tightening system 210, and re-engage the fasteners of pull tabs 240A and 250B with fasteners 240B and 250B.

In some preferred embodiments, a first cord and a second cord are substantially the same length (i.e., ±5%) or have exactly the same length so that a user could advantageously achieve uniform tightening using each of the first and second cords.

It should also be appreciated that a fastener (e.g., on a lateral support) could be complementary to both a fastener of a second lateral support and a fastener of a pull tab. Viewed from another perspective, a fastener could be configured, sized and dimensioned to fasten with two or more fasteners that are complementary, either simultaneously or sequentially.

Some exemplary cord guides and cord lobes of some contemplated tightening systems can be found in U.S. Patent Application Publication Nos. 2009/0192425, 2012/0232450, and 2012/0245502, and U.S. Pat. Nos. 7,001,348 and 8,142, 377. In some preferred embodiments, an adjustment of a tightening system from a first configuration to a second configuration is effective to render an elastic lumbar support effectively inelastic (or not stretchable beyond 110%) of its original length when the brace is worn by a wearer.

As shown in FIG. 2B, brace 200 can include a first cord guide cover 260 and a second cord guide cover 270 that encloses first cord guide base 212 and second cord guide base 214. The cord guide covers can be included for aesthetic purposes, or to better protect tightening mechanism 210 from the environment or tampering.

While the description herein is generally directed towards braces having elastic portions configured to extend across the lower back of a wearer, it is contemplated that an elastic support and an inelastic tightening mechanism extending across it could be included in any suitable brace, including for example, leg braces, ankle braces, wrist braces, or knee braces.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Thus, specific adjustable braces have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A brace that provides support to a lower spine of a wearer's body, comprising:
   a lumbar support positioned between left and right lateral supports, the lumbar support having an elastic portion that is sufficiently elastic such that the lumbar support stretches to conform to the wearer's body when the brace is wrapped around a torso of the wearer, and the left and right lateral supports are releasably secured to one another at or near an abdomen;
   an inelastic tightening system including at least a first cord that extends over a length of an outer surface of the elastic portion of the lumbar support and is thread through at least a first cord guide; and
   wherein the inelastic tightening system is configured to reduce an effective elasticity of the lumbar support and apply a force to a lower back of the wearer's body when tightened, and wherein the elastic portion is stretchable by at least 10% in a first direction, and the elastic portion is configured to return to its original length when the inelastic tightening system is in a loosened configuration.

2. The brace of claim 1, wherein the tightening system further comprises a second cord guide, and wherein the first and second cord guides are coupled to opposite sides of the lumbar support.

3. The brace of claim 2, wherein the entire lumbar support is disposed between the first and second cord guides.

4. The brace of claim 2, further comprising a second cord, and wherein a portion of the first cord is fed about the first cord guide and a portion of the second cord is fed about the second cord guide.

5. The brace of claim 1, wherein the left lateral support comprises an inelastic material and an elastic material.

6. The brace of claim 5, wherein the elastic material has a width of between 3 inches and a width of the lumbar support.

7. The brace of claim 1, wherein the tightening system further comprises a second cord guide, and wherein the first cord guide is coupled to the left lateral support, and wherein the second cord guide is coupled to the right lateral support.

8. The brace of claim 1, wherein the elastic portion of the lumbar support is sufficiently elastic such that the lumbar support stretches when the brace is applied to the wearer's body, and returns to its original shape when removed from the wearer's body.

9. The brace of claim 1, wherein the elastic portion is stretchable by at least 15% in the first direction when applied by the wearer.

10. The brace of claim 1, further comprising a fastener configured to removably couple the left lateral support to the right lateral support.

11. The brace of claim 1, wherein the elastic portion is stretchable to increase from an original length to X times the original length when the tightening system is not used, and wherein the elastic portion is stretchable to increase from the original length to no more than 0.2X times the original length when the tightening system is used.

12. The brace of claim 1, wherein the elastic portion is configured to extend across a sagittal plane of the wearer when applied to the wearer.

13. A brace that provides support to a body of a wearer, comprising:
   a central support having an elastic portion that is sufficiently elastic to stretch to conform to the wearer's body when the brace is wrapped around the body of the wearer;
   first and second supports coupled to the central support, such that the central support is disposed between the first and second supports;
   wherein the first support is made at least in part from a first inelastic material; and
   an inelastic tightening system including at least a first cord that threads through at least a first cord guide and extends over a length of an outer surface of the elastic portion of the central support, wherein the inelastic tightening system is configured to reduce an effective elasticity of the elastic portion across the length and apply a force to a portion of the body of the wearer when tightened, and wherein the elastic portion is capable of stretching at least 10% more from its original length when worn with the inelastic tightening system in a loosened configuration than when worn with the tightening system in a tightened configuration.

14. The brace of claim 13, wherein the tightening system further comprises a second cord guide, and wherein the first and second cord guides are coupled to opposite sides of the central support.

15. The brace of claim 14, wherein the entire central support is disposed between the first and second cord guides.

16. The brace of claim 13, wherein the tightening system further comprises a second cord guide, and wherein the first cord guide is coupled to the first support, and wherein the second cord guide is coupled to the second support.

17. The brace of claim 13, wherein the elastic portion of the central support has a width of between 3 inches and a width of the central support.

18. The brace of claim 13, wherein the elastic portion is stretchable by at least 10% in a first direction when applied by the wearer.

19. The brace of claim 13, further comprising a fastener configured to removably couple the first support to the second support.

20. The brace of claim 13, wherein the elastic portion is stretchable to increase from an original length to X times the original length when the tightening system is not used, and wherein the elastic portion is stretchable to increase from the original length to no more than 0.2X times the original length when the tightening system is used.

\* \* \* \* \*